United States Patent [19]

Foster et al.

[11] Patent Number: 5,516,413

[45] Date of Patent: May 14, 1996

[54] RUGGED ELECTRODE FOR ELECTROCHEMICAL MEASUREMENTS AT HIGH TEMPERATURES AND PRESSURES

[75] Inventors: John P. Foster, Monroeville; Richard J. Jacko, Murrysville Boro, both of Pa.

[73] Assignee: Westinghouse Electric Corporation, Pittsburgh, Pa.

[21] Appl. No.: 115,380

[22] Filed: Sep. 1, 1993

[51] Int. Cl.$^6$ ............................................. G01N 27/30
[52] U.S. Cl. .................................. 204/435; 204/404
[58] Field of Search .................................... 204/435

[56] References Cited

U.S. PATENT DOCUMENTS

| | | | |
|---|---|---|---|
| 2,706,710 | 4/1955 | Ladisch | 204/435 |
| 2,846,386 | 8/1958 | Ingruber | 204/408 |
| 3,272,731 | 9/1966 | Hutchison et al. | 204/435 |
| 3,461,055 | 8/1969 | Staunton | 204/435 |
| 4,116,798 | 9/1978 | Magar et al. | 204/435 |
| 4,210,508 | 7/1980 | Bergson | 204/430 |
| 4,500,413 | 2/1985 | Taylor et al. | 204/435 |
| 4,636,292 | 1/1987 | Fetes et al. | 204/435 |
| 4,725,399 | 2/1988 | McCulloch et al. | 376/247 |
| 5,234,570 | 8/1993 | Taylor et al. | 204/435 |
| 5,262,038 | 11/1993 | Indig et al. | 204/435 |

OTHER PUBLICATIONS

Agrawal et al, "A Silver–Silver Chloride Reference Electrode for the High Temperature and High Pressure Electrochemistry", *Corrosion*, 1977, pp. 418–419.

*Primary Examiner*—T. Tung

[57] ABSTRACT

A high temperature-high pressure electrode for electrochemical potential measurement has a high temperature probe comprising an oxidized zirconium alloy tube member having an electroconductive core which includes a liquid electrolyte and a porous plug held in place by an oxidized zirconium alloy tube and end plug with an axial bore extending therethrough. The electroconductive core can comprise a liquid electrolyte of soaked zirconia sand and a second porous plug. In another embodiment, the zirconia sand is replaced by a surface oxidized zirconium alloy rod with grooves which extend between ends for containment of the liquid electrolyte. This embodiment also contains a second porous plug. In a modification of the latter embodiment, there is a bore in the proximal end of the surface oxidized rod which communicates with the grooves to provide electrical continuity. A Teflon sleeve forms an annular seal between the proximal end of the oxidized rod and the oxidized tube.

22 Claims, 2 Drawing Sheets

RUGGED ELECTRODE FOR ELECTROCHEMICAL MEASUREMENTS AT HIGH TEMPERATURES AND PRESSURES

BACKGROUND OF THE INVENTION

1. Field of the Invention

This invention relates to an improved high temperature-high pressure electrode. It is directed to apparatus for electrochemical potential measurements in a high temperature-high pressure environment with particular application in electrochemical potential measurements for monitoring corrosion in hostile environments such as nuclear power plants.

2. Background Information

The majority of electrode kinetic studies in high temperature aqueous systems have employed external reference electrodes which are maintained at ambient temperature. External reference electrodes have their electroactive elements at ambient temperature outside the high temperature system. Communication between the electroactive element and the high temperature zone is made with a non-isothermal (cooled) KCl solution electrolyte bridge. The KCl electrolyte bridge provides contact with the test solution at high temperature and pressure inside the autoclave system. Usually, the cooled salt bridge and the external reference electrode operate at the same pressure as the high temperature vessel.

Many different electroactive reference elements such as Ag/AgCl, Hg/Hg$_2$Cl$_2$ and Cu/saturated CuSO$_4$ can be employed in the inner compartment of the pressure balanced system. For most applications, the Ag/AgCl electrode has been preferred. The Ag/AgCl half-cell is established when a Ag/AgCl element is immersed in a chloride solution. This results in the equilibrium

$$Ag+Cl^-=AgCl+e^- \quad E°=-0.222 \text{ V} \tag{1}$$

In a 0.1N KCl solution at 25° C., the potential is 288 mV vs. the standard hydrogen electrode. The use of electro-chemical sensors for the monitoring of electrode potentials of metallic components in high temperature-high pressure aqueous environments is still not a straightforward technique, although research into the establishment of suitable electrochemical corrosion testing methods for application in high temperature pressurized systems is already 15 to 20 years old. The experimental difficulties are basically related to the combined presence of high temperature and high pressure, which produce leaks. Electrodes are normally constructed with glass or Teflon. However, electrochemical potential measurements at temperatures greater than 290° C. are difficult because glass reacts with high temperature water and Teflon looses its structural strength. For temperatures greater than 120° C. glass melts. For temperatures greater than 290° C. the creep resistance of Teflon is so low that it has no structural integrity.

Other methods to take measurements in high temperatures have also been tried. U.S. Pat. No. 4,725,399 to McCulloch et al. discloses a probe for measuring heat which includes an elongated rod fitted within a sheath, and a plurality of annular recesses formed on the surface of the rod in a spaced-apart relationship to form annular chambers that are resistant to heat flow.

U.S. Pat. No. 4,636,292 discloses an electrode for electrochemical measurements in aqueous solutions at high temperature with a casing comprising sintered particles of aluminum oxide, zirconium oxide or other electrically-insulating material which is inert to water.

Stanford Research International (SRI) has developed an external pressure balanced Ag/AgCl electrode that does not use Teflon in the high temperature section of the electrode. The electrode has been successfully used to temperatures up to 340° C. A porous zirconia plug is attached to the ceramic zirconia tube by placing the plug inside a zirconia tube that has a hole in the distal end of the tube in the direction of the tube axis of rotation. The plug is pushed to the closed end. The tube is then packed with coarse zirconia sand soaked in KCl. Another zirconia plug is placed in the open end of the tube to retain the sand. The zirconia sand section represents the "outer" high temperature electrode chamber. The internal zirconia plug separates the "outer" chamber from the "inner" low temperature electrode chamber. The "inner" low temperature chamber is filled with KCl solution. Normally, 0.1N or 0.01N KCl solution is used. Chlorine contamination of the test solution is minimized by using a porous plug. The fine porosity of the porous plug allows electrical conductivity to be established between the Ag/AgCl element and the test sample. Further, the bottom porous plug restricts chloride transport from the electrode into the test solution. In the case of high temperature water, zirconia plugs are used because zirconia is insoluble.

The SRI electrode has four disadvantages. The first disadvantage is that the electrode is very delicate. The high temperature zirconia ceramic tube easily fractures. Zirconia tube fractures have been observed to occur due to handling or thermal shock. Heatup thermal shock occurs whenever the heatup rates are greater than about 100° F./h. Cooldown thermal shock occurs whenever the test system pressure or temperature limit switches trip and the autoclave naturally air cools down from operating temperatures greater than 290° C.

The second disadvantage is that the zirconia ceramic tube of the SRI electrode can develop fine porosity holes with extended use in high temperature and high pressure water environments. Electrodes fabricated with CaO stabilized zirconia tubes exhibited porosity in the region of the tube exposed to the high temperature-high pressure PWRRCS primary water (i.e., distilled water with impurity additions of boron and lithium). Zirconia ceramic tubes are typically fabricated using stabilization impurities. Examples of these impurity additions are CaO, MgO and Y$_2$O$_3$. The impurities are typically in the range of 3% to 12%. Note that these impurities may be associated with second phases that are susceptible to primary water corrosion. The CaO stabilized zirconia tubes exhibited through wall porosity after 1.5 to 2 months of exposure. Similar behavior is expected with Y$_2$O$_3$ stabilized zirconia. Autoclave tests with Y$_2$O$_3$ stabilized zirconia samples exhibited weight loss. This demonstrates that the material is dissolving in the water solution.

The third disadvantage is the chloride contamination of the test solution. Zirconia sand is used in the high temperature KCl bridge to retain the zirconia porous plug. The maximum packing density of the sand is about 65%. When the electrode is heated to the test temperature the KCl thermally expands and is forced through the zirconia porous plug into the test solution. In the case of primary water testing, chloride contamination is undesirable. One embodiment of the invention reduces this contamination by a factor of 5 relative to the SRI electrode.

The fourth disadvantage of the SRI electrode is that a post test room temperature calibration cannot be performed, when the test temperature is above about 325° C. After cooldown, the inner low temperature chamber usually contains a large volume of gas and a small volume of liquid KCl. The gas is attributed to the zirconia sand and the decrease in gas solubility at intermediate temperatures. The zirconia sand has a large surface area which could absorb a large quantity of dissolved gas at high temperature. Evidently, when the electrode is cooled down from the test temperature the gas is released and exceeds the solution solubility limit. At room temperature, the gas disrupts electrical continuity and a room temperature calibration to see how the electrode potential has changed cannot be performed.

A novel improved electrode is needed which incorporates rugged high temperature-high pressure electrode components and preferably eliminates the zirconia sand.

OBJECTS OF THE INVENTION

Accordingly, it is an object of this invention to provide rugged high temperature-high pressure electrode components which can be used at temperatures greater than 290° C. at high pressures.

It is an object of this invention to provide such electrode components which are corrosion resistant.

It is another object of this invention to design electrode components that have high toughness, strength and ductility.

It is a further object of the invention to provide such an electrode which can be calibrated at room temperature after testing.

It is still another object of the invention to provide such electrodes which preferably do not utilize zirconia sand.

These objects and others are satisfied by the following invention.

SUMMARY OF THE INVENTION

This invention relates to an improved high temperature electrode. This high temperature electrode is adapted for electrochemical potential measurements in a high temperature and high pressure environment and comprises a zirconium alloy tube having an oxide coating on the inner and outer surfaces, an electroconductive core including a liquid electrolyte within the tube and plug means at the distal end of the tube to contain the liquid electrolyte within the tube. The plug means comprises a porous zirconia plug secured in the distal end of the tube by a zirconium alloy plug having an oxide coating on the inner and outer surface and an axial bore therethrough. The zirconium alloy is selected from the group consisting of Zircaloy-4, Zircaloy-2 and Zirlo. In one embodiment of the invention, the electroconductive core comprises zirconia sand and a liquid electrolyte. A second porous plug is at the proximal end of the tube filled with the sand and the liquid electrolyte. In a preferred embodiment, the electroconductive core comprises a rod which reduces the volume of liquid electrolyte required and eliminates the need for zirconia sand, thus alleviating the gas contamination problem. Preferably, the rod, which is a zirconium alloy, the same as the tube, with an oxide coating, substantially fills the tube, and has grooves in its outer surface, preferably helical grooves, which are filled with the liquid electrolyte. A second porous plug is situated on top of the rod at the proximal end of the tube. In another embodiment of the invention, the rod has a bore extending generally axially from its proximal end which communicates with the grooves on the proximal end of the oxidized rod to insure electrolyte continuity. In this latter embodiment of the invention, a Teflon sleeve forms an annular seal between the proximal end of the tube and the proximal end of the rod in place of the second porous plug.

These and other objects of the present invention will be more fully understood from the following description of the invention in reference to the illustrations appended herein.

DESCRIPTION OF THE PREFERRED EMBODIMENT

Figure 1:
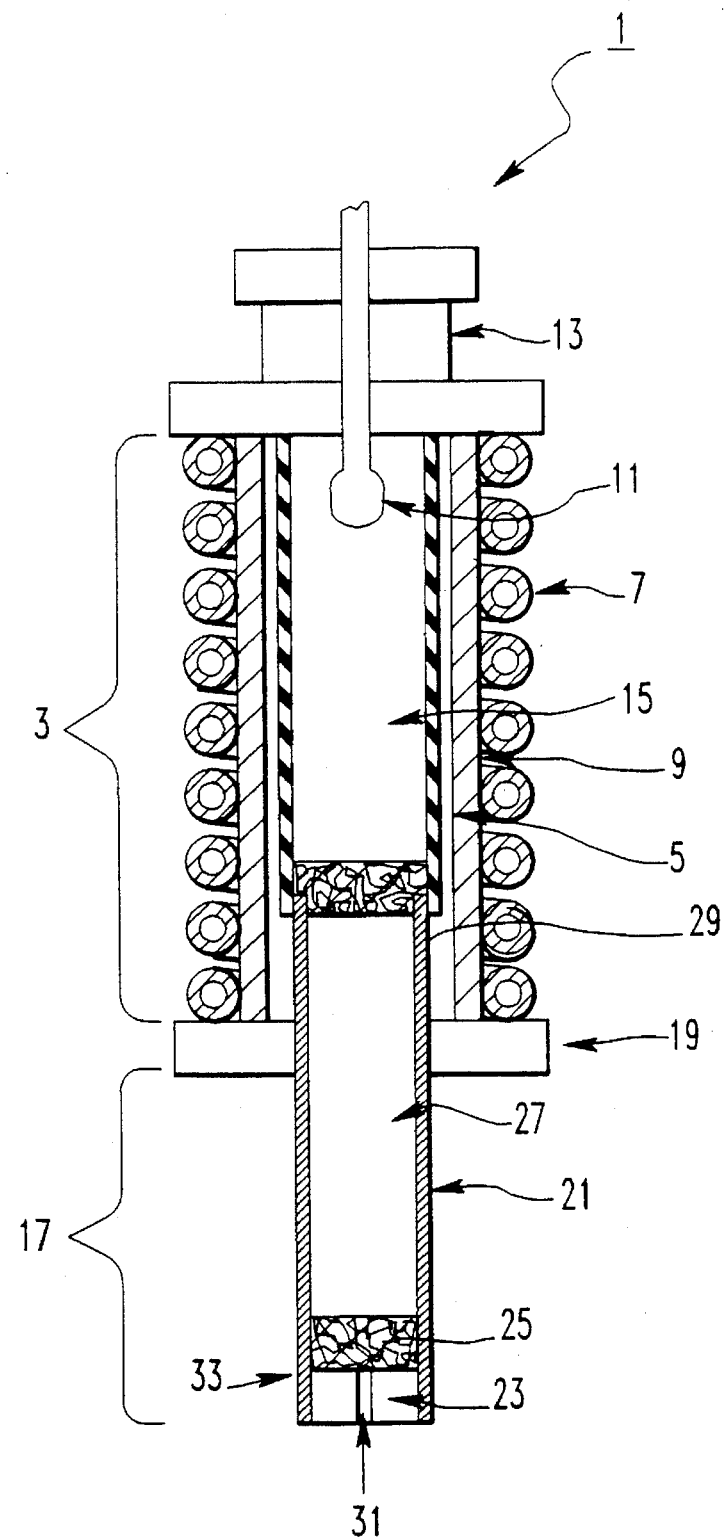
FIG. 1 is a longitudinal section through an Ag/AgCl electrode incorporating the invention.

An improved electrode has been designed which incorporates rugged high temperature electrode components in several embodiments. As an example only, the invention will be described using a Zircaloy-4 alloy of zirconium, although other alloys of zirconium such as Zircaloy-2 or Zirlo can be used. Zircaloy-2 is a zirconium alloy containing (by weight) about 1.2%–1.7% tin, 0.07%–0.20% iron, 0.05%–0.15% chromium and 0.03%–0.08% nickel; and Zircaloy-4 is a zirconium alloy containing (by weight) about 1.2%–1.7% tin, 0.12%–0.18% iron and 0.05%–0.15% chromium. Reference may be had to U.S. Pat. No. 4,584,030 for a discussion of Zircaloy materials and fabrication processes. Zirlo is a zirconium alloy containing (by weight) about 0.5%–2.0% niobium, 0.7%–1.5% tin, 0.07%–0.14% iron and 0.03%–0.14% of nickel and/or chromium. Reference may be had to U.S. Pat. No. 5,230,758 for a discussion of Zirlo materials and fabrication processes. The selected electrolyte solution can be either KCl or water, although KCl will be described herein. FIG. 1 illustrates a longitudinal section through an Ag/AgCl electrode incorporating one embodiment of the invention. The system 1 includes a low temperature section 3 that consists of a Teflon tube 5 inside a stainless steel tube 7 surrounded with a copper water cooling coil 9. The Ag/AgCl electrode 11 extends through a reducing union 13 to be immersed in KCl solution 15 surrounded by a water cooled Teflon tube. The high temperature section 17 (probe) extends down from the Teflon tube. A reducing union 19 connects the electrode to the test apparatus. The high temperature section (probe) 17 measures electrochemical potentials in hostile environments which include high temperature corrosive solutions such as hot water and radioactive environments.

The high temperature section (probe) 17 of system 1 is made up of a Zircaloy-4 (Zr-4) tube 21 and a Zr-4 end plug 23 welded to the Zr-4 tube 21. The Zr-4 tube 21 and end plug 23 are oxidized inside and out to provide electrical insulation and corrosion resistance. The Zr-4 tube and end plug exhibit high toughness, strength and ductility. The end plug 23 which is welded onto the tube secures a zirconia porous plug 25 in the distal end of the oxidized Zr-4 tube. The tube is filled with zirconia sand soaked in 0.1N KCl solution 27. Another porous plug 29 is placed above the KCl soaked sand in the proximal end of the oxidized Zr-4 tube. The end plug 23 has an axial capillary bore 31 which allows ions from the test solution to move for electrical continuity. The porous plugs help restrict solution transfer and help prevent contamination of the KCl solution.

EXAMPLE 1

The Zr-4 tube 21 and end plug 23 were fabricated using standard 0.360 inch OD×0.023 inch wall standard nuclear fuel rod tubing and a standard 0.360 inch OD end plug. The end plug 23 was welded to the tube 21. The Zr-4 tube and end plug were swagged to an outside diameter of about 0.282 inches for compatibility with existing electrode components. A bore 31 about 0.012 inches is drilled through the end plug 23 of the tube 21 preferably axially and the end plug is machined flat. The tube 21 and end plug 23 are oxidized for about 25 to 75 hours at a temperature of about 595° C. to 625° C. in air. Careful control of both the preoxidation surface (i.e., surface preparation) and temperature control of the oxidation process are required to produce a relatively thick stoichiometric tan color oxide with a thickness of 2 to 4 mils. Just prior to oxidation the tube and welded end plug are degreased with acetone and etched with a solution of 45% $HNO_3$: 45% $H_2O$: 10% HF. Etching provides a fresh, uniform and clean surface for surface oxidation. Temperature control of the oxidation process is very important. The oxidation process should be performed at temperatures high enough to permit economical operation but low enough to prevent spalling of the oxide. Thus, the process temperature should be maintained between about 400° C. and about 1000° C. and more preferably between about 595° C. and about 625° C. As the temperature decreases from 595° C. the oxidation kinetics decrease exponentially so that very long oxidation times will be required to produce a sufficiently thick oxide. In the case of temperatures above about 625° C. (e.g., in the range of 1000° to 1200° C.), the oxide becomes susceptible to spalling with increasing temperature. The resulting oxidized tube-end plug has the properties of a corrosion resistant electrical insulator and has high toughness, strength and ductility.

A very closely fit porous zirconia plug 25 is placed at the closed end of the welded, oxidized Zr-4 tube-end plug 21, 23 by inserting the zirconia porous plug 25 into the oxidized tube-end plug and pushing it to the distal end. The position of the porous zirconia plug is fixed by an interference fit between the plug and the oxidized Zr-4 tube. The tube 21 has a slight reduction taper 33 in the vicinity of the end plug 23 to retain the porous plug 25. The fit between the zirconia porous plug and the tube is much tighter with the Zr-4 tube than with the zirconia ceramic tube. This is possible because tubing quality, straightness and ID tolerances are significantly smaller for the Zr-4 tube than the zirconia ceramic tube. Secondly, the surface match between the porous zirconia plug and the oxidized Zr-4 end plug is perfect because both are machined flat surfaces. In the case of the SRI electrode, the surface match between the porous plug and the zirconia tube is poor because the inside of the zirconia tube is a hemisphere and the plug is a flat surface. The tube is then packed with zirconia sand soaked in 0.1N KCl solution 27. Another porous plug 29 is placed at the proximal end of the oxidized tube.

Experimental test data have been obtained with the improved electrode. Three electrodes were placed in one autoclave with primary water and heated to a temperature of 325° C. The three electrodes were a SRI Ag/AgI electrode, an improved Ag/AgCl electrode (embodiment 1 of this disclosure) and a standard hydrogen electrode. The SRI and improved Ag/AgCl electrodes were connected to the standard hydrogen electrode. About 800 hours of test data were obtained. The electrodes were initially tested in deionized water with additions of 1200 ppm boron and 2 ppm lithium. After 382 hours the test solution was changed to pure deionized water. The results show that the electrode potential of the improved Ag/AgCl electrode is similar to the SRI Ag/AgCl electrode.

Another embodiment of the electrode containing the improved high temperature chamber eliminates the zirconia sand.

Figure 2:
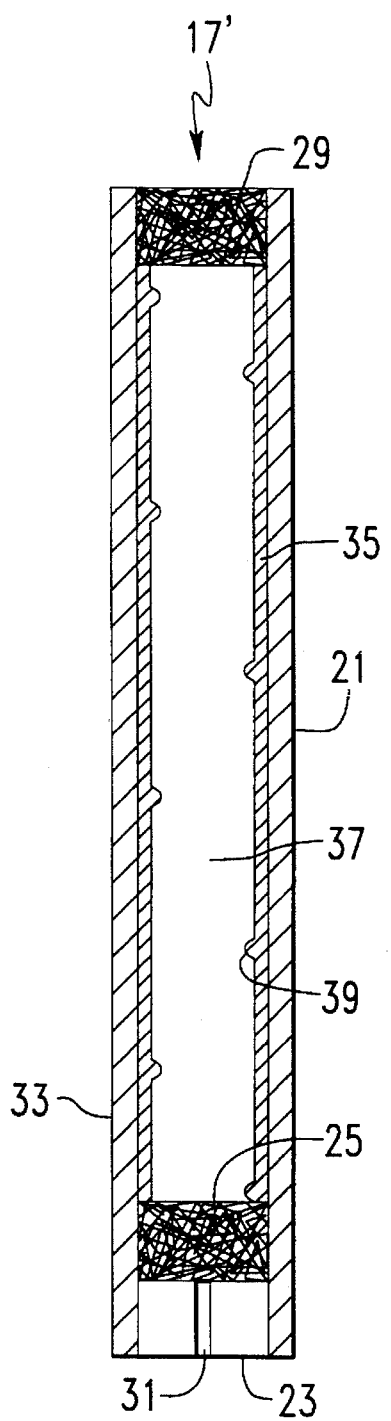
FIG. 2 is a longitudinal section through the high temperature section of an electrode in another embodiment of the invention.

This embodiment is shown by FIG. 2. In the probe 17', the KCl solution volume 35 is reduced by placing a rod 37 made from an oxidized alloy of zirconium, such as Zr-4, Zr-2, or Zirlo (preferably Zr-4) in the tube 21. The rod 37, the tube 21 and the tube-end plug 23 which are of the same material are oxidized for electrical insulation and corrosion protection. There is a porous zirconia plug 25 in the bottom tapered part 33 of the tube held in place by the zirconium alloy end plug 23. Grooves 39, which are preferably helical, extend along the outer surface of the rod. The liquid electrolyte fills the space between the tube, the rod and the grooves. The rod reduces the volume of liquid electrolyte solution so that only a small amount of 0.1N KCl solution is displaced from the electrode due to thermal expansion during heat-up to the test temperature. Another zirconia porous plug 29 is placed above the oxidized grooved Zr-4 rod. The tube has a tapered distal end 33 with an axial bore 31 in the end plug 23.

EXAMPLE 2

As an example of the probe in accordance with the above experiment, the dimensions of the oxidized rod are 14 inches long with a diameter of 0.282 inches to give a close fit between the rod 37 at tube 21. The helical grooves 39 in the rod 37 have a radius of about 15 mils. The rod reduces the volume of liquid electrolyte solution so that only a small amount of 0.1N KCl solution is displaced from the electrode due to thermal expansion during heat-up to test temperature.

Figure 3:
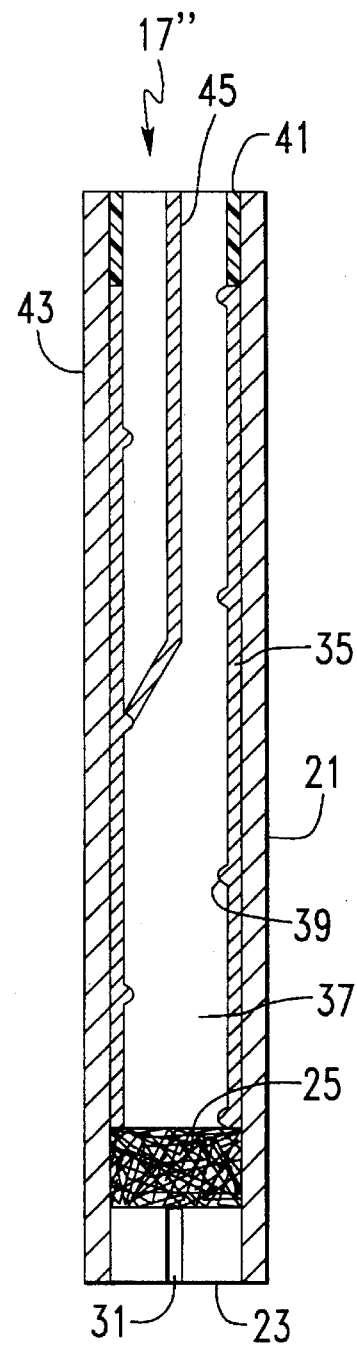
FIG. 3 illustrates another embodiment of the invention in the high temperature section of the electrode.

The third embodiment is shown by FIG. 3. In the probe 17', the oxidized rod 37 with helical grooves 39 has a Teflon sleeve 41 which forms an annular seal between the proximal end face 43 of the oxidized rod 37 and the oxidized tube 21. The oxidized rod has a bore 45 extending generally axially and radially outwardly from the proximal end face 43 of the rod 37 to intersect the helical grooves 39 in the proximal section of the rod to insure electrical continuity. There is a porous plug 25 in the oxidized tube 21 and on top of the oxidized end plug 23 at the distal end of the tube. The end plug 23 has an axial bore 31.

EXAMPLE 3

As an example of the probe in accordance with the above experiment, the dimensions of the oxidized rod are 14 inches long with a diameter of 0.282 inches to give a close fit between the rod 37 at tube 21. The helical grooves 39 in the rod 37 have a radius of about 15 mils. Bore 45 has a diameter of about 0.032 mils.

The newly developed sturdy tube and rod which does not crack or develop fine porous holes has also solved a long standing need in the field. Not only will this high temperature-high pressure improved electrode withstand temperatures between about 290° C. and about 500° C. without cracking or developing holes in the oxidized Zr-4 tube and end plug, it also reduces chloride contamination of the test solution and allows the post test room temperature calibration to be performed because the electrical continuity has not been disrupted by gas. Chloride contamination of the test solution is reduced because the solid oxidized Zr-4 rod reduces the liquid KCl volume in the oxidized Zr-4 tube. Typically, zirconia sand can be packed up to a maximum density of 65%. This results in a KCl cross-sectional area of 0.0153 $inch^2$. On the other hand, in the case of the example 2 embodiment of this disclosure an 8 mil diametral clearance is associated with a KCl cross-sectional area of 0.0029 inch². The rod reduces the KCl by a factor of 5.3 relative to the SRI electrode design. A reduction of the liquid KCl in the high temperature components of the electrode reduces chloride contamination of the test solution. When the electrode is heated to the test temperature, the liquid KCl thermally expands, and is forced through the porous zirconia plug into the test solution. A reduction of the KCl in the electrode decreases the quantity forced through the porous plug into the test solution. In conventional electrodes, after testing at temperatures above about 325° C., the inner low temperature chamber usually contains a large volume of gas and a small volume of liquid KCl. The gas is attributed to the zirconia sand and the decrease in gas solubility at intermediate temperatures. The zirconia sand has a large surface area which can absorb a large quantity of dissolved gas at high temperatures.

While specific embodiments of the invention have been described in detail, it will be appreciated by those skilled in the art that various modifications and alternatives to these details can be developed in light of the overall teachings of the disclosure. Accordingly, the particular arrangements disclosed are meant to be illustrative only and not limiting as to the scope of the invention which is to be given the full breadth of the appended claims.

We claim:

1. An improved probe adapted for electrochemical potential measurements in a high temperature and pressure environment, said probe comprising:

a zirconium alloy tube member having an electrically insulating oxide coating on an inner surface and on an outer surface thereof;

an electroconductive core including a liquid electrolyte contained within said tube member; and plug means at a distal end of said tube member containing said liquid electrolyte within said tube member.

2. The probe of claim 1 wherein said plug means comprises a porous zirconia plug secured in said distal end of said tube member by a zirconium alloy end plug having an oxide coating on an inner surface facing the porous zirconia plug and on an outer surface thereof and having an axial bore therethrough.

3. The probe of claim 2, wherein said zirconium alloy used for said tube member and said end plug is selected from the group consisting of Zircaloy-4, Zircaloy-2 and Zirlo.

4. The probe of claim 3, wherein said electroconductive core comprises zirconia sand and said liquid electrolyte.

5. The probe of claim 4, wherein a second porous zirconia plug is situated at a proximal end of said tube member above said zirconia sand.

6. The probe of claim 3 wherein said electroconductive core comprises a rod member inserted in said tube member adjacent said porous zirconia plug and said liquid electrolyte is located between said tube member and said rod member.

7. The probe of claim 6, wherein said rod member is made of the same material as said tube member.

8. The probe of claim 7, wherein at least one of said rod member and said tube member has a groove extending between ends thereof which is filled with said liquid electrolyte.

9. The probe of claim 8, wherein said groove is helical.

10. The probe of claim 8, wherein a Teflon sleeve forms an annular seal between a proximal end of said rod member and a proximal end of said tube member.

11. The probe of claim 10, wherein said rod member has an end face and a bore extending generally axially and radially outwardly from said end face and communicating with said groove.

12. The probe of claim 6, wherein a porous zirconia plug is situated at said proximal end of said tube member above said rod member.

13. The probe of claim 3, wherein the electrolyte is an aqueous solution.

14. The probe of claim 2, wherein said surfaces of said tube member and said end plug are degreased and chemically etched to provide fresh, uniform and clean surfaces for surface oxidation and then oxidized to form an electrically insulating coating.

15. An improved rugged electrode for use at high temperatures and pressures, comprising:

(a) a low temperature section comprising:
      a water cooled housing;
      a Teflon tube within the housing containing a liquid electrolyte; and
      an immersed electrode in the liquid electrolyte; and (b) a probe comprising:
      a zirconium alloy tube member having an electrically insulating oxide coating on inner and outer surfaces thereof, said tube member extending from said Teflon tube in said water cooled housing;
      porous plug means at a distal end of said tube member containing said liquid electrolyte within said tube member; and
      a zirconium alloy plug having an oxide coating on an inner surface facing said porous plug and on an outer surface thereof and having an axial bore therethrough securing said porous plug means in said distal end of said tube member.

16. The probe of claim 15, wherein the oxide coatings on said surfaces have a 2 mil to 4 mil thickness.

17. The improved electrode of claim 15, further comprising an electroconductive core contained in said tubular member, said core comprising zirconia sand and said liquid electrolyte.

18. The improved electrode of claim 15, further comprising an electroconductive core, said core comprising a zirconium alloy rod member inserted in said tube member adjacent said porous plug means with the liquid electrolyte between said tube member and said rod member.

19. The improved electrode of claim 18, wherein said zirconium alloy rod member is oxidized and of the same material as said tube member and at least one of said rod member and said tube member has grooves extending between ends thereof filled with liquid electrolyte.

20. The improved electrode of claim 19, wherein said oxidized rod has an end face and a bore extending generally axially and radially outwardly from said end face and communicating with said groove.

21. The improved electrode of claim 20, wherein a Teflon sleeve forms an annular seal between a proximal end of said rod member and a proximal end of said tube member.

22. The improved electrode of claim 21, wherein the zirconium alloy is selected from the group consisting of Zircaloy-2, Zircaloy-4 and Zirlo and the electrolyte is an aqueous KCl solution.

* * * * *